US010376547B2

(12) United States Patent
Mercati et al.

(10) Patent No.: US 10,376,547 B2
(45) Date of Patent: Aug. 13, 2019

(54) COMPOSITION COMPRISING BEE PRODUCTS (71) Applicant: ABOCA S.P.A SOCIETÀ AGRICOLA, Sansepolcro (IT)

(72) Inventors: Valentino Mercati, Sansepolcro (IT); Luca Rampoldi, Sansepolcro (IT)

(73) Assignee: ABOCA S.P.A. SPCIETÀAGRICOLA, Sansepolcro AR (IT)

( * ) Notice: Subject to any disclaimer, the term of this patent is extended or adjusted under 35 U.S.C. 154(b) by 124 days.

(21) Appl. No.: 15/121,582

(22) PCT Filed: Mar. 10, 2015

(86) PCT No.: PCT/IB2015/051722
§ 371 (c)(1),
(2) Date: Aug. 25, 2016

(87) PCT Pub. No.: WO2015/140666
PCT Pub. Date: Sep. 24, 2015

(65) Prior Publication Data
US 2016/0361368 A1 Dec. 15, 2016

(30) Foreign Application Priority Data
Mar. 18, 2014 (IT) .............. RM2014A0138

(51) Int. Cl.
| | |
|---|---|
| *A61K 8/02* | (2006.01) |
| *A61K 35/644* | (2015.01) |
| *A61K 9/02* | (2006.01) |
| *A61K 47/44* | (2017.01) |
| *A61Q 17/00* | (2006.01) |
| *A61Q 19/00* | (2006.01) |
| *A61K 8/92* | (2006.01) |
| *A61K 8/98* | (2006.01) |
| *A61K 9/00* | (2006.01) |
| *A61K 9/20* | (2006.01) |
| *A61K 36/886* | (2006.01) |
| *A61K 8/97* | (2017.01) |
| *A61K 36/185* | (2006.01) |
| *A61Q 1/06* | (2006.01) |

(52) U.S. Cl.
CPC .......... *A61K 35/644* (2013.01); *A61K 8/0229* (2013.01); *A61K 8/922* (2013.01); *A61K 8/927* (2013.01); *A61K 8/97* (2013.01); *A61K 8/988* (2013.01); *A61K 9/0036* (2013.01); *A61K 9/02* (2013.01); *A61K 9/2068* (2013.01); *A61K 36/185* (2013.01); *A61K 36/886* (2013.01); *A61K 47/44* (2013.01); *A61Q 1/06* (2013.01); *A61Q 17/00* (2013.01); *A61Q 19/00* (2013.01); *A61Q 19/001* (2013.01); *A61K 2800/5922* (2013.01)

(58) Field of Classification Search
None
See application file for complete search history.

(56) References Cited

U.S. PATENT DOCUMENTS

| | | | |
|---|---|---|---|
| 7,887,857 B1 | 2/2011 | Johnson | |
| 8,663,710 B1 | 3/2014 | Johnson | |
| 8,940,342 B1 | 1/2015 | Johnson | |
| 9,078,839 B1 * | 7/2015 | Pascal, Sr. | ............ A61K 8/922 |
| 2007/0166253 A1 | 7/2007 | Kostick et al. | |
| 2007/0196298 A1 | 8/2007 | Kostick et al. | |
| 2009/0130220 A1 | 5/2009 | Johnson | |
| 2011/0142775 A1 | 6/2011 | Kostick et al. | |

FOREIGN PATENT DOCUMENTS

| | | |
|---|---|---|
| CN | 101 417 064 | 3/2011 |
| CN | 102 397 224 | 4/2012 |
| RU | 2146920 C1 * | 3/2000 |
| RU | 2146920 C1 * | 3/2000 |

OTHER PUBLICATIONS

International Search Report for PCT/IB2015/051722, five pages (dated Oct 2015).
Written Opinion of the ISA for PCT/IB2015/051722, six pages (dated Oct 2015).
Attama et al. "Further characterization of theobroma oil-beeswax admixtures as lipid matrices for improved drug delivery systems" *European Journal of Pharmaceutics and Biopharmaceutics*, vol. 64, No. 3, pp. 294-306 (Nov. 2006).

* cited by examiner

*Primary Examiner* — Nannette Holloman
(74) *Attorney, Agent, or Firm* — Sterne, Kessler, Goldstein & Fox P.L.L.C.

(57) ABSTRACT

The present application relates to a composition consisting of honey, beeswax and cocoa butter, characterized by a melting temperature of 36±3° C., pharmaceutical, veterinary or cosmetic formulations comprising or coated by said composition, and processes for the preparation of said composition and said formulations.

26 Claims, 1 Drawing Sheet

COMPOSITION COMPRISING BEE PRODUCTS

This application is the U.S. national phase of International Application No. PCT/IB2015/051722, filed 10 Mar. 2015, which designated the U.S. and claims priority to Italian Application No. RM2014A000138, filed 18 Mar. 2014; the entire contents of each of which are hereby incorporated by reference.

The present application relates to a composition consisting of honey, beeswax and cocoa butter, characterized by a melting temperature of 36±3° C., pharmaceutical, veterinary or cosmetic formulations comprising or coated by said composition, and processes for the preparation of said composition and said formulations.

STATE OF THE PRIOR ART

The importance of bee products, both from a therapeutic and cosmetic standpoint, is known from ancient times. Bee products are known for their important therapeutic use in the field of protection from irritations, inflammations and in the reduction of infection risk, in the dermatological field and in ophthalmology, and exert a protective role on skin and mucous membranes.

Honey, for instance, is known for its cicatrizing, antimicrobial, protective, antioxidant properties. Interest about honey is also linked to the fact that many of its protective therapeutic effects are due to mechanical mechanisms of action and are therefore particularly safe.

Honey is made up almost exclusively (95-99% of dry matter) of sugars, and simple sugars, glucose, fructose, constitute 85-95% thereof. Moreover, it contains traces of proteins, albumin, globulin, amino acids and mineral salts, traces of organic and inorganic salts and other components depending on the plant from which it derives; in addition, it is rich in phenolic compounds and other antioxidants, and of polyphenols.

It is widely reported in the literature that honey has probiotic, antibacterial, antioxidant and antimicrobial activities.

Beeswax constitutes honeycomb cells and is mainly comprised of even- and odd-chain saturated and unsaturated hydrocarbons, monoesters of palmitic, oleic and hydroxypalmitic acids. There are chemical analyses apt to distinguish virgin beeswax from wax adulterated by paraffin.

For some components of beeswax, protective and antiinflammatory effects at the level of gastric mucous membrane have been found, with effects on both indomethacin- and ethanol-induced ulcers. Such results hint at a protective chemico-physical action mechanism due to the lipophilic character of wax, that might well be added to the aforedescribed benefits of honey.

The use of beeswax and honey together is known, for topical applications. For instance, they are used in Middle East Countries together with olive oil for the treatment of skin lesions, even serious ones. However, in this type of preparations beeswax and honey are dispersed in olive oil and their preparation is extemporaneous, as the composition obtained is not easy to preserve. Moreover, the use of these formulations requires patients immobility for more or less lengthy times to enable the product to remain on the site of interest.

In order to make bee products application/administration more practical, to reduce transport, storage, preservation problems and increase the compliance thereof, it would be extremely advantageous to combine the properties of wax and honey into a solid product.

The necessary features of the product have to be such as to enable mixing of the two components, the hydrophilic one (honey) and the lipophilic one (beeswax), and to enable mixture melting at about 37° C. Moreover, also a good spreadability, along with a high safety in case of oral administration, have to be guaranteed.

The mixing of hydrophilic and lipophilic components usually occurs by use of surfactants and/or emulsifiers (e.g., polyethylene glycols derivatives) in order to enable dispersion of lipophilic substances in the lipid mass.

In particular, Chinese Patent Application CN102764224 describes a mixture containing 16 to 20 parts of jojoba fat, 8 to 10 parts of cocoa butter, 10 to 14 parts of sunflower seed oil, 6 to 8 parts of beeswax, 1 to 3 parts of hyaluronic acid, 2 to 4 parts of coenzyme Q10 and 1 to 2 parts of honey.

The composition described in the document is a balm, therefore a semisolid formulation, and is a mainly lipophilic formulation, in which the amount of hydrophilic product is minimal. As mentioned hereto, emulsifying agents such as acetylated lanoline and others are normally used in the literature in order to incorporate honey into a lipophilic substrate.

To be able to set up a solid formulation useful for topical or internal use in or on mammals, humans included, the formulation must have a melting temperature close to body temperature, and therefore a melting temperature close to 37° C. and, to be able to be used for internal use, including an oral intake, it must have a high safety making it suitable to this type of administration.

Therefore, it is of interest to develop solid compositions containing bee products such as wax and honey, free of surfactants and/or emulsifiers, with a melting temperature close to 37° C., in order to facilitate a topical and/or internal administration of the bee products.

SUMMARY OF THE INVENTION

For carrying out the present invention, the authors tried to find a way to be able to incorporate, in an amount of up to 30 parts by weight on 100, a hydrophilic product such as honey into a lipophilic matrix of natural substances comprising also beeswax.

Since a product that could be safely administered, even orally, was desired, the authors of the present invention tried to find a substance, to be added to honey and beeswax, that were natural and safe from an oral and toxicological standpoint.

Cocoa butter has a known oral safety, both under the pharmaceutical toxicological profile and the alimentary profile. It is substantially free of substances having a biological activity and its lipid content does not compromise blood triglyceride profile. Moreover, it has a good substance release profile and is widely used on mucous membranes. However, cocoa butter, above all when used in large amounts in mixtures, exhibits a phenomenon well-known to the technician in the field, which is represented by polymorphism.

It has long been known that various cocoa butter polymorphs do exist; the native form of pure cocoa butter is represented by polymorph beta, having a melting temperature of between 34° C. and 38° C.

It is known in the literature (e.g., Enrico Ragazzi "*Lezioni di tecnica farmaceutica*" Ed. Libreria Cortina 1978), that the thermal treatment of cocoa butter in the course of the preparation of molten masses (e.g., of suppositories) is an extremely critical step, and that the temperature at which this fat is treated must not be higher than 38° C. as, when cocoa butter is treated at temperatures higher than 38° C., at cooling the polymorphism phenomenon occurs, i.e. the coexistence of cocoa butter in various crystalline forms, each one having a different melting point.

Forms α and γ, in particular, have a melting temperature respectively at 22 and 18° C., and an overheating of cocoa butter leads to the presence of crystals in the above-mentioned forms, remarkably lowering the melting point of cocoa butter, therefore making it unsuitable to be present in high percentages in formulations that must have a final melting temperature close to 37° C.

However, the Inventors surprisingly discovered that cocoa butter, when co-melt with suitable proportions of beeswax and honey at temperatures between 65 and 90° C., does not exhibit, in the cooling and solidification stage, the formation of polymorphs α and γ. This data is evident from FIG. 1, in which it is clearly seen that the melting profile of pure cocoa butter and that of a composition consisting of
from >0≤30 parts by weight of honey
from >0≤17 parts by weight of beeswax
from ≥65 parts by weight of cocoa butter
for a total of 100 parts by weight
are substantially overlapping and that no melting peaks are present at the temperatures of polymorphs α and γ.

The result, entirely unexpected, therefore enables to incorporate a high amount of hydrophilic substances, such as honey, into a lipophilic matrix consisting of at least 65 parts by weight of cocoa butter, and from >0≤17 parts by weight of beeswax, obtaining a product that has a melting temperature of 36±3° C.

To the ends of the present invention, by >0 it is meant different from 0, preferably at least ≥0.1. The value >0 as indicated in the patent may therefore be replaced anywhere by the value ≥0.1.

This result may be obtained without particular preparatory contrivances, by heating cocoa butter and beeswax concomitantly (co-melting) at the melting temperatures of beeswax, which are at about 70-80° C.

The composition described herein is therefore useful for the treatment and the protection of skin and mucous membranes, given the known properties of honey and beeswax; moreover, thanks to the presence of honey, hydrophilic, it can also be used as a base or a coating for pharmaceutical, veterinary or cosmetic formulations, as it enables homogeneous incorporation of hydrophilic material.

In fact, by respecting the dosages described herein, compositions or formulations having the following characteristics are obtained
melting at a temperature close to body temperature of most mammals (36±3° C.)
capable of releasing therapeutic substances on the mucous membranes thanks to the presence of honey
without any evident mass dishomogeneity, therefore making pointless the aid of substances such as emulsifiers and/or surfactants.

Hence, object of the invention are:
a composition consisting of
from >0≤30 parts by weight of honey
from >0≤17 parts by weight of beeswax
from ≥65 parts by weight of cocoa butter
for a total of 100 parts by weight.
a base or a coating for a pharmaceutical, veterinary, alimentary or cosmetic formulation consisting of the above-described composition;
a pharmaceutical, veterinary, alimentary or cosmetic formulation comprising the composition as presented in the present description and one or more active ingredients and/or adjuvants and/or excipients;
a process for the preparation of the composition as presented in the present description, comprising the following steps
a. subjecting to co-melting, at a temperature comprised between 55° C. and 90° C., from >0≤30 parts of honey; from >0≤17 parts of beeswax; from ≥65 parts of cocoa butter on a total of 100 parts by weight
b. cooling after pouring into suitable moulds or containers; and
a process for the preparation of the pharmaceutical, veterinary or cosmetic formulation as presented in the present description comprising the following steps:
a. subjecting to co-melting, at a temperature comprised between 55° C. and 90° C., from >0≤30 parts of honey; from >0≤17 parts of beeswax; from ≥65 parts of cocoa butter on a total of 100 parts by weight;
b. adding to the mixture prepared in a. one or more active ingredients and/or adjuvants and/or excipients so that said mixture prepared in a. represents at least 70%, at least 80% at least 90% or at least 95% by weight of the mixture obtained in step b.
c. cooling after pouring into suitable moulds or containers.

DETAILED DESCRIPTION OF THE FIGURES

Figure 1:
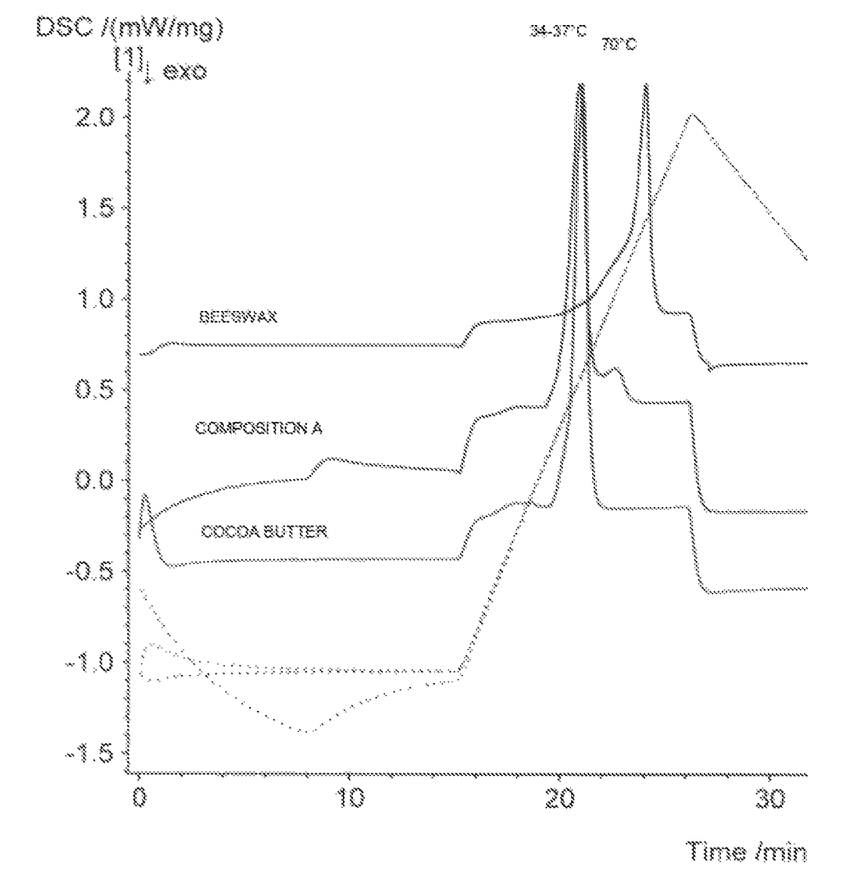
FIG. 1. Top to bottom, there are respectively reported the thermograms of:
beeswax, showing a melting peak at about 70° C., denoted by "BEESWAX"
composition according to the invention, showing a melting peak at 37° C., denoted by "COMPOSITION A"
pure cocoa butter, showing a melting peak at 34-37° C., denoted by "COCOA BUTTER"

There are reported: on the X-axis the time, on the Y-axis the energy administered to the sample, expressed as mW/mg.

The FIGURE clearly shows that the composition of the invention, prepared by simple standard techniques such as those described in the detailed section, at temperatures well above 38° C., has a melting peak at about 37° C.; no melting peak is present for any of cocoa butter polymorphs α and γ, and beeswax melting peak at 70° C. is also lost, beeswax clearly being completely incorporated into the composition of the invention.

In the FIGURE, it may be observed that the melting peaks of cocoa butter—pure and when formulated in Composition A—are coincident, confirming the maintaining of cocoa butter polymorph form beta.

DETAILED DESCRIPTION OF THE INVENTION

The present description relates to a composition consisting of
from >0≤30 parts by weight of honey
from >0≤17 parts by weight of beeswax
from ≥65 parts by weight of cocoa butter
for a total of 100 parts by weight.
Provided that these proportions are respected, all combinations of possible relative amounts of the three components are possible, and each individual combination is part of the present description.

Therefore, object of the present description is any combination between

>0, >0.1, >0.2, >0.3, >0.4, >0.5, >0.6, >0.7, >0.8, >0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 parts by weight of honey and any intermediate number among the above-specified ones, >0, >0.1, >0.2, >0.3, >0.4, >0.5, >0.6, >0.7, >0.8, >0.9, 1, 2, 3, 4, 5, 6, 7, 8, 9, 10, 11, 12, 13, 14, 15, 16, 17 parts by weight of beeswax and any intermediate number among the above-specified ones, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and <100 parts by weight of cocoa butter and any intermediate number among the above-specified ones when the sum among these three elements is 100, wherein the sum of beeswax and honey does not exceed 35 parts by weight on 100.

Any of these combinations is to be considered as described in the present description, since sufficient data are provided to easily and quickly calculate the possible combinations.

In one embodiment of the invention, the parts by weight of honey are ≥0.1, or are ≥0.5, or are ≥1, or are ≥5; or are ≥10; or are ≥15; or are ≥20; or are ≥25 and greater than or equal to any intermediate number among those indicated, or even ≥26, ≥27, ≥28, ≥29, and ≤30.

As already mentioned, the composition of the present invention enables a high incorporation of honey into a mainly lipophilic base resulting in a mass free of dishomogeneities, therefore making pointless the aid of substances such as emulsifiers and/or surfactants.

The composition according to the invention therefore does not comprise surfactants, nor emulsifiers.

According to further embodiments of the invention, the parts by weight of beeswax are ≥0.1, or are ≥0.5, or are ≥1, or are ≥5; or are ≥10; or are ≥15 or greater than or equal to any intermediate number among those indicated, or even ≥16 and ≤17.

Part of the invention are embodiments wherein the parts by weight of honey are ≥0.1, or are ≥0.5, or are ≥1, or are ≥5; or are ≥10; or are ≥15; or are ≥20; or are ≥25 and the parts by weight of beeswax are ≥0.1, or are ≥0.5, or are ≥1, or are ≥5; or are ≥10; or are ≥15 provided that, as evident from the above definition, the sum of beeswax and honey never exceeds 35 parts by weight on 100.

According to a further embodiment, the parts by weight of cocoa butter are ≥70; or are ≥75; or are ≥80; or are ≥85, until reaching values anyhow <100.

In particular, the composition according to the invention comprises embodiments wherein the parts by weight of honey are ≥0.1, or are ≥0.5, or are ≥1, or are ≥5; or are ≥10; or are ≥15; or are ≥20; or are ≥25 and the parts by weight of beeswax are ≥0.1, or are ≥0.5, or are ≥1, or are ≥5; or are ≥10; or are ≥15 provided that, as evident from the above definition, the sum of beeswax and honey never exceeds 35 parts by weight on 100, and ≥70; or ≥75; or ≥80; or ≥85 parts by weight of cocoa butter.

In the present invention unadulterated natural beeswax, and pure, unadulterated bee honey and cocoa butter are used. The compositions in the above-described embodiments have a melting temperature of 36±3° C. Said temperature is particularly advantageous, as it enables compositions to be in a solid or semisolid state at temperatures close to the body temperatures of most mammals.

In a particular embodiment, the composition is characterized by having a melting temperature of 36±2° C., in particular a melting temperature of about 36, about 37, about 38° C.

For human use, embodiments with a melting temperature of about 37° C. are preferred.

According to the present description, there are described herein embodiments of the composition as above-indicated and as claimed, characterized in that they are substantially free of cocoa butter polymorphs α and/or γ.

The term "substantially free" means that peaks related to these polymorphs are not detectable in thermograms of the composition of the invention, or that anyhow such polymorphs are not detectable in the composition of the invention. The term "substantially free" is used since conventional measurement means might not detect traces of polymorphs. In other terms, the above-mentioned polymorphs are not detectable by DSC (Differential Scanning Calorimetry).

The absence or the substantial absence of these polymorphs enables the maintaining of the melting temperature of the composition at 36±3° C., a temperature that would not be possible in compositions comprising at least 65 parts on 100 by weight of cocoa butter should cocoa butter be present as polymorphs α and/or γ.

Given the constituent elements thereof and their melting temperature, the compositions of the invention are suitable for a topical or internal pharmaceutical or veterinary use for treatments of protection of the skin or of the mucous membranes thanks to the barrier effect and to the mucoadhesive abilities of the composition, provided by the bee products contained therein.

By "barrier effect" (BE) it is meant the ability of a compound or of a substance to create a protective film on a cell surface, such as, e.g., the mucous membrane or the skin.

The composition of the invention can, by virtue of the barrier and mucoadhesive effect given thereto by the bee products contained therein, facilitate the repair of damaged mucosal or skin tissue with entailed restoration of healthy and elastic skin or mucous membrane, or even simply carry out a protective effect on skin and mucous membranes from external agents, or drugs, etc.

Moreover, as indicated above, the bee products contained in the composition also have antibacterial and antiinflammatory effects known from the literature, which are well-matched to the barrier effect and the mucoadhesive properties.

Therefore, object of the invention is the composition of the invention as described and claimed herein for use in the protective, lenitive or curative treatment of the skin or mucous membranes.

By "lenitive or curative treatment" it is meant, for instance, the treatment of superficial lesions, insect bites, allergic states, sores, rashes, infections, inflammations, burns, abrasions.

The skin lesions according to the present invention can be lesions that may involve also tissue underlying the skin and in which no open wounds are present, or can be lesions with open wounds or even burns or other types of lesions.

By "skin lesions not implying the presence of open wounds", according to the present description, are meant those lesions in which the superficial layer of the skin, and the underlying layers, though not being wounded, are particularly fragile, irritated and damaged.

Non-limiting examples of this type of lesions are represented by first-degree burns, first-degree decubitus lesions, pressure lesions, newly cicatrized rashes, wounds or burns, irritations, erythemas, insect bites.

Given the presence of antibacterial and antiinflammatory components in the bee products contained in the composition of the invention, the composition could also be directly used for the treatment of skin lesions or burns or inflammations or infections by topical or oral, rectal, vaginal administration.

The compositions of the invention could then be used for the treatment or the prevention of skin lesions not implying the presence of open wounds, or in the prevention or slowing down of worsenings of the same, or in the treatment of skin lesions with open wounds.

When the compositions of the invention are used for the protection of the skin, the application thereof will be topical. The composition could be prepared, for instance, in the form of stick.

According to another embodiment, the compositions of the invention could be used, thanks to their mucoadhesive and barrier effect, for the protection of mucous membranes.

In these cases the administration may be topical, for all those mucous membranes on which a topical administration is possible, or may be internal (e.g., buccal, rectal, vaginal, nasal mucous membrane) or oral in the cases in which they be, e.g. intestinal or gastric mucous membranes.

In this case as well said protection could be a preventive protection, e.g. in all those cases envisaging the administration of drugs which have the side effect of attacking the mucous membranes, or in those patients exhibiting conditions of recurring irritation of the same. In other cases, the protection could instead be a protection for curative purposes or in order to avoid the worsening of irritated or partially compromised mucous membranes.

The compositions for the protection of mucous membranes could therefore be made in the form of soft capsule, hard or soft gelatine, tablet, coated tablet, suppository, vaginal ovule.

In the form of suppository there can, e.g., be used compositions according to the invention consisting of 5 to 17 parts by weight of beeswax, 5 to 25 parts by weight of honey, and 65 to 90 parts by weight of cocoa butter, for a total of 100 parts.

Hereinafter there are provided non-limiting examples of compositions of the invention apt to be made in the form of suppository:

| | EXAMPLES OF COMPOSITIONS IN THE FORM OF SUPPOSITORIES/VAGINAL OVULES | | | | | | | | |
|---|---|---|---|---|---|---|---|---|---|
| | parts | | | | | | | | |
| Substance | Comp. 1 | Comp. 2 | Comp. 3 | Comp. 4 | Comp. 5 | Comp. 6 | Comp. 7 | Comp. 8 | Comp. 9 |
| Cocoa butter | 65 | 70 | 75 | 80 | 85 | 69 | 73 | 82 | 85 |
| Beeswax | 15 | 10 | 10 | 10 | 10 | 15 | 9 | 7 | 5 |
| Honey | 20 | 20 | 15 | 10 | 5 | 16 | 18 | 11 | 10 |

As mentioned above, the composition of the invention could be made also for an oral administration, e.g. in the form of hard or soft gelatine capsule, or of tablet.

The technician in the field will know how to select the best proportions among the components of the composition as described herein to make the above-described forms for oral administration.

By way of a non-limiting example, suitable for oral administration are embodiments wherein the composition consists of 2 to 17 parts by weight of beeswax, 5 to 30 parts by weight of honey, and 65 to 90 parts by weight of cocoa butter for a total of 100 parts by weight of composition.

Hereinafter, there are provided non-limiting examples of compositions of the invention apt to be made for oral administration:

| | EXAMPLES OF COMPOSITIONS FOR ORAL USE | | | | | | | | |
|---|---|---|---|---|---|---|---|---|---|
| | Parts | | | | | | | | |
| Substance | Comp. 1 | Comp. 2 | Comp. 3 | Comp. 4 | Comp. 5 | Comp. 6 | Comp. 7 | Comp. 8 | Comp. 9 |
| Cocoa butter | 65 | 70 | 75 | 80 | 85 | 66 | 73 | 82 | 85 |
| Beeswax | 16 | 15 | 10 | 10 | 10 | 4 | 9 | 7 | 5 |
| Honey | 19 | 15 | 15 | 10 | 5 | 30 | 18 | 11 | 10 |

As to the use of the composition in the protection of the skin, the invention can be made for topical administration in the form of lip sticks (balms) or cutaneous sticks.

The technician in the field will know how to choose the best proportions among the components of the composition as described herein to make the above-described forms for topical administration.

By way of a non-limiting example, suitable for topical administration are embodiments wherein the composition consists of 4 to 17 parts by weight of beeswax, 10 to 25 parts by weight of honey, and 65 to 85 parts by weight of cocoa butter for a total of 100 parts by weight of composition.

Hereinafter, there are provided non-limiting examples of compositions of the invention apt to be made for topical administration:

| EXAMPLES OF COMPOSITIONS IN THE FORM OF STICK | | | | | | | | | |
|---|---|---|---|---|---|---|---|---|---|
| | parts | | | | | | | | |
| Substance | Comp. 1 | Comp. 2 | Comp. 3 | Comp. 4 | Comp. 5 | Comp. 6 | Comp. 7 | Comp. 8 | Comp. 9 |
| Cocoa butter | 65 | 70 | 75 | 80 | 68 | 72 | 75 | 78 | 76 |
| Beeswax | 14 | 16 | 11 | 5 | 11 | 16 | 12 | 7 | 9 |
| Honey | 21 | 14 | 14 | 15 | 21 | 12 | 13 | 15 | 15 |

The composition according to the present description could be made in the form of pharmaceutical composition or of medical device according to any one of the classes described in Directive 93/42/EEC on medical devices (comprising also substances and not only "devices" in the mechanical sense of the term), or in any suitable form according to the regulatory provisions of the Country in which said composition will be produced.

The compositions of the invention are therefore useful for their barrier effect properties and mucoadhesion properties in all those cases in which the protection of skin or mucous membranes is needed or desirable, those may be cases in which a drug that attacks mucous membranes or skin has to be administered, therefore in order to prevent or limit the damaging action of the drug or active ingredient, or in those cases in which the protection of a partially compromised skin or mucous membrane is preferable or desirable so as to enable a better and quicker healing thereof, defending it from further aggressions, or in those cases in which an individual has a chronic disorder in which skin or mucous membranes sustain irritations or alterations, therefore a barrier effect can prevent or limit damages on the skin or the mucous membrane.

The invention also relates to a method for the treatment or for the prevention of the onset or the worsening of skin lesions not implying the presence of open wounds (e.g., by stick) or for the treatment of open wounds (e.g., by solidifying the composition on a device such as a gauze, a plaster or the like so as to make a medicated device) wherein such method comprises one or more applications of the composition of the invention once or more per day on the concerned part.

The application of the composition, for instance, could be repeated whenever needed, or once, twice, thrice, four or more times per day in general.

Object of the present invention is also a method for the protective (preventive or curative) treatment of the skin or mucous membranes, providing the administration of the composition of the present invention to a patient in need thereof. Such administration could also be concomitantly with the administration of other drugs.

A non-limiting example of the method of treatment and/or of prevention of the skin or mucous membranes could comprise the administration of a daily dosage, subdivided into a single dose or plural doses, of the composition according to the present description, for a period of time of between one and six weeks, e.g. of between three and six weeks or even for a period of time higher than six weeks, in accordance with the judgment of the treating doctor.

Such administration could precede the administration of the drug even for a prolonged period, so as to the health state of the skin or of the mucous membrane to be treated.

The treating doctor will know how to establish both the most appropriate dosage and the administration times, also on the basis of the patient's health state, weight, sex and age.

As indicated above, the composition can then be used for internal use, i.e. for oral, vaginal or rectal use, or topically, and therefore can be made in the form of suppository, vaginal ovule, film, cutaneous stick, lip balm (stick), film (deposited, e.g., on a medicated plaster or gauze), soft capsule, hard or soft gelatine, tablet.

Due to its characteristics of being able to homogeneously and uniformly incorporate hydrophilic substances, given by the presence of honey, it also homogeneously and uniformly incorporated into the lipophilic matrix, the composition of the invention is very advantageously suitable as a completely natural base, without any additive, for pharmaceutical, veterinary or cosmetic formulations, medical devices and foods for special medical purposes (medical foods), and as such represents another aspect of the invention.

Furthermore, the composition of the invention could be employed by the technician in the field also as coating of pharmaceutical or veterinary tablets, using the techniques well-known and described in the state of the art.

Moreover, object of the invention is also a pharmaceutical, veterinary or cosmetic formulation or a medical device comprising the composition as described herein and one or more active Ingredients and/or adjuvants and/or excipients.

Even in the case of formulations, all those formulations that do not contain emulsifiers and/or surfactants are preferred, since, due to the characteristics of the composition of the invention, such ingredients are unnecessary for the incorporation of active ingredients in a homogeneous form.

As already mentioned, the composition of the present invention enables a high incorporation of honey into a mainly lipophilic base, resulting in a mass free of dishomogeneities, thereby making pointless the aid of substances such as emulsifiers and/or surfactants also for the incorporation of hydrophilic active ingredients.

In order to maintain the above-described characteristics for the composition of the invention, the formulation according to the invention comprises a high percentage of the above-described composition, in particular those embodiments wherein the formulation comprises at least 70%, at least 80% at least 90% or at least 95% by weight of said composition are preferred.

As mentioned above, the high percentage of composition in the formulations allows to have formulations having a melting temperature of 36±3° C. or of 36±2° C.

What described above for the compositions is to be considered as comprised in the description of the formulations; therefore, in the formulations of the invention all possible above-described embodiments of the composition will be used.

In one embodiment of the invention, the parts by weight of honey of the base composition are ≥0.1, or are ≥0.5, or are ≥1, or are ≥5; or are ≥10; or are ≥15; or are ≥20; or are ≥25 and any intermediate number among those indicated, or even ≥26, ≥27, ≥28, ≥29, and ≤30.

According to further embodiments of the invention, the parts by weight of beeswax in the base composition used are ≥0.1, or are ≥0.5, or are ≥1, or are ≥5; or are ≥10; or are ≥15 and any intermediate number among those indicated, or also ≥16 and ≤17.

Embodiments wherein in the base composition (including also the embodiment as coating) used for the preparation of the formulations the parts by weight of honey are ≥0.1, or are ≥0.5, or are ≥1, or are ≥5; or are ≥10; or are ≥15; or are ≥20; or are ≥25 and the parts by weight of beeswax are ≥0.1, or are ≥0.5, or are ≥1, or are ≥5; or are ≥10; or are ≥15, are part of the invention provided that, as evident from the above definition, the sum of beeswax and honey never exceeds 35 parts by weight on 100.

According to a further embodiment, the parts by weight of cocoa butter in the base composition used are ≥70; or are ≥75; or are ≥80; or are ≥85, until reaching values anyhow <100.

In particular, the formulations of the invention comprise embodiments of the base composition wherein the parts by weight of honey are ≥0.1, or are ≥0.5, or are ≥1, or are ≥5; or are ≥10; or are ≥15; or are ≥20; or are ≥25 and the parts by weight of beeswax are ≥0.1, or are ≥0.5, or are ≥1, or are ≥5; or are ≥10; or are ≥15 provided that, as evident from the above definition, the sum of beeswax and honey never exceeds 35 parts by weight on 100, and ≥70; or ≥75; or ≥80; or ≥85 parts by weight of cocoa butter.

As for the compositions, given the solid state of the formulations comprising the composition, these can be made, for instance, in the form of suppository, vaginal ovule, cutaneous stick, lip balm, lipstick, capsule, hard or soft gelatine, tablet, coated tablet, film (deposited, e.g., on a medicated plaster or gauze).

In case of a film deposited on a medicated gauze or plaster, e.g. a classic medical device would be had.

When made in the form of suppository or vaginal ovule, the formulation may comprise from 80% to 99% by weight of the above-described base composition and the remainder as active ingredients, plus, optionally, adjuvants and/or excipients.

The expert in the field could select, among the various embodiments of the composition of the invention, those forms he/she deems more suitable for the preparation of suppositories or vaginal ovules.

By way of a non-limiting example of the embodiment, indicated above, it could be used as formulation base a composition according to the invention consisting of 5 to 17 parts by weight of beeswax, 5 to 25 parts by weight of honey, and 65 to 90 parts by weight of cocoa butter on 100 parts by weight of composition.

For instance, as formulation base there could be used a composition as defined above, wherein beeswax is 10 to 15 parts by weight.

In one embodiment, the composition described in the two preceding paragraphs could be used, wherein honey is 10 to 20 parts by weight.

Then, in the formulation active ingredients, both hydrophilic and lipophilic ones, could be introduced; those could be pharmaceutical, cosmetic active ingredients, or alimentary substances of natural, synthetic or semisynthetic origin. Besides active ingredients, excipients and/or adjuvants could optionally be added.

Hereinafter, non-limiting examples of base composition are provided for formulations in the form of suppositories or vaginal ovules according to the invention.

| FORMULATIVE BASE EXAMPLES FOR SUPPOSITORIES/VAGINAL OVULES | | | | | | | | | |
|---|---|---|---|---|---|---|---|---|---|
| | parts | | | | | | | | |
| Substance | Base 1 | Base 2 | Base 3 | Base 4 | Base 5 | Base 6 | Base 7 | Base 8 | Base 9 |
| Cocoa butter | 65 | 70 | 75 | 80 | 85 | 69 | 73 | 82 | 85 |
| Beeswax | 15 | 10 | 10 | 10 | 10 | 15 | 9 | 7 | 5 |
| Honey | 20 | 20 | 15 | 10 | 5 | 16 | 18 | 11 | 10 |

These base compositions are mixed with the active ingredients or active ingredients plus adjuvants and/or excipients, into final formulations containing at least 70%, at least 75%, at least 80%, at least 85%, at least 90% at least 95% of base composition.

By way of example, and by no way of limitation, the above bases can be mixed, to give the formulations of the invention, with the active ingredients or the active ingredients plus adjuvants and/or excipients, in the following proportions:

| FORMULATIVE EXAMPLES FOR SUPPOSITORIES/VAGINAL OVULES | | | | | | | | | |
|---|---|---|---|---|---|---|---|---|---|
| | parts | | | | | | | | |
| Substance | Form. 1 | Form. 2 | Form. 3 | Form. 4 | Form. 5 | Form. 6 | Form. 7 | Form. 8 | Form. 9 |
| Cocoa butter | 65 | 70 | 75 | 80 | 85 | 69 | 73 | 82 | 85 |
| Beeswax | 15 | 10 | 10 | 10 | 10 | 15 | 9 | 7 | 5 |

FORMULATIVE EXAMPLES FOR SUPPOSITORIES/VAGINAL OVULES
-continued

| Substance | Form. 1 | Form. 2 | Form. 3 | Form. 4 | Form. 5 | Form. 6 | Form. 7 | Form. 8 | Form. 9 |
|---|---|---|---|---|---|---|---|---|---|
| | | | | parts | | | | | |
| Honey | 20 | 20 | 15 | 10+ | 5 | 16 | 18 | 11 | 10 |
| Active ingredients* | 16 | 11 | 3 | 11 | 4 | 9 | 3 | 9 | 8 |

Therefore, e.g. in formulation 1 the relative percentages are: base composition abt 86%, active ingredients* abt 14%; in 2 are: base composition abt 90%, active ingredients* abt 10%; in 3 are: base composition abt 97%, active ingredients* abt 3%; in 4 are: base composition abt 90%, active ingredients* abt 10%; in 5 are: base composition abt 95%, active ingredients* abt 5%; in 6 are: base composition abt 92% active ingredients* abt 8%; in 7 are: base composition abt 97%, active ingredients* abt 3%; in 8 are: base composition abt 92%, active ingredients* abt 8%; in 9 are: base composition abt 93%, active ingredients* abt 7%.

*In the examples provided above, the term "active ingredients" may also be replaced by the term "active ingredients plus adjuvants and/or excipients".

As already mentioned above, the formulations can also comprise adjuvants and/or excipients.

According to another embodiment, the formulation may be a formulation for oral use, like, e.g., a hard or soft gelatine capsule, tablet, coated tablet.

When made as indicated above, the composition for oral use may comprise 75% to 99% by weight of composition of the invention (also referred to herein as "base" composition) and the remainder as active ingredients plus, optionally, adjuvants and/or excipients.

In this case as well, the technician in the field will know how to easily select, among the possible embodiments of the composition of the invention, which composition be the most suitable to make pharmaceutical formulations for oral use as those described above.

By way of a non-limiting example of the embodiment indicated above, it may be used as base for a formulation for oral use in the form of hard or soft gelatine capsule, tablet, coated tablet a composition according to the invention, consisting of 2 to 17 parts by weight of beeswax, 5 to 30 parts by weight of honey, and 65 to 90 parts by weight of cocoa butter on 100 parts by weight of composition.

For instance, a composition as defined above, wherein beeswax is about 0.1, 0.5, 5, 10, 15 parts by weight, could be used as base for the formulation.

In one embodiment, there could be used a composition described in the two preceding paragraphs, wherein honey is 10 to 30 parts by weight.

Moreover, active ingredients could be introduced in the composition, both hydrophilic and lipophilic ones, that could be pharmaceutical, cosmetic active ingredients, or alimentary substances of natural, semisynthetic or synthetic origin. As indicated above, besides active ingredients, excipients and/or adjuvants could optionally be added.

Hereinafter, non-limiting examples are provided of base for formulations for oral use as defined above according to the invention.

FORMULATIVE BASE EXAMPLES FOR COMPOSITIONS FOR ORAL USE

| Substance | Base 1 | Base 2 | Base 3 | Base 4 | Base 5 | Base 6 | Base 7 | Base 8 | Base 9 |
|---|---|---|---|---|---|---|---|---|---|
| | | | | Parts | | | | | |
| Cocoa butter | 65 | 70 | 75 | 80 | 85 | 66 | 73 | 82 | 85 |
| Beeswax | 16 | 15 | 10 | 10 | 10 | 4 | 9 | 7 | 5 |
| Honey | 19 | 15 | 15 | 10 | 5 | 30 | 18 | 11 | 10 |

These base compositions are mixed with the active ingredients, or active ingredients plus adjuvants and/or excipients, into final formulations containing at least 70%, at least 75%, at least 80%, at least 85%, at least 90% at least 95% of base composition.

In one embodiment, instead of being mixed with the active ingredients or with the active ingredients plus adjuvants and/or excipients, the base described herein will be used as such as coating of said active ingredients, and optionally excipients and/or adjuvants.

By way of example, and by no way of limitation, the above bases can be mixed with the active ingredients or the active ingredients plus adjuvants and/or excipients (or coat the active ingredients or active ingredients plus adjuvants and/or excipients) in the following proportions:

| FORMULATIVE EXAMPLES FOR FORMULATIONS FOR ORAL USE | | | | | | | | | |
|---|---|---|---|---|---|---|---|---|---|
| | parts | | | | | | | | |
| Substance | Form. 1 | Form. 2 | Form. 3 | Form. 4 | Form. 5 | Form. 6 | Form. 7 | Form. 8 | Form. 9 |
| Cocoa butter | 65 | 70 | 75 | 80 | 85 | 66 | 73 | 82 | 85 |
| Beeswax | 16 | 15 | 10 | 10 | 10 | 4 | 9 | 1 | 5 |
| Honey | 19 | 15 | 15 | 10 | 5 | 30 | 18 | 11 | 10 |
| Active ingredients* | 32 | 28 | 6 | +14 | 14 | 30 | 22 | 18 | 24 |

Therefore, for instance in formulation 1 the relative percentages are: base composition abt 76%, active ingredients* abt 24%; in 2 are: base composition abt 78%, active ingredients* abt 22%; in 3 are: base composition abt 94%, active ingredients* abt 6%; in 4 are: base composition abt 88%, active ingredients* abt 12%; in 5 are: base composition abt 88%, active ingredients* abt 12%; in 6 are: base composition abt 77% active ingredients* abt 23%; in 7 are: base composition abt 82%, active ingredients* abt 18%; in 8 are: base composition abt 85%, active ingredients* abt 15%; in 9 are: base composition abt 81%, active ingredients* abt 18%.

*In the examples provided above, the term "active ingredients" may also be replaced by the term "active ingredients plus adjuvants and/or excipients".

As already mentioned above, the formulations can also comprise adjuvants and/or excipients.

According to a further embodiment, the formulation according to claim may be a formulation for topical use and may be a film, a cutaneous stick or a lip balm (including a lipstick).

When made for topical use, the formulation may comprise 80% to 99% by weight of said composition and the remainder as active ingredients plus adjuvants and/or excipients, or as sole adjuvants and/or excipients.

By way of a non-limiting example of the embodiment indicated above, it may be used as base for a formulation for topical use like the above-described ones a composition according to the invention, consisting of 4 to 17 parts by weight of beeswax, 10 to 25 parts by weight of honey, and 65 to 85 parts by weight of cocoa butter for 100 parts by weight of composition.

For instance, a composition as defined above, wherein beeswax is 5 to 16 parts by weight, could be used as formulation base.

In one embodiment, a composition described in the two preceding paragraphs, wherein honey is 14 to 25 parts by weight, could be used.

In this case as well, in the formulation there could be introduced active ingredients, both hydrophilic and lipophilic ones, which could be pharmaceutical, cosmetic active ingredients, or alimentary substances of natural, synthetic or semisynthetic origin.

In the particular case of cutaneous sticks or lip balms (sticks), the formulation could be a formulation solely for medical use, or could also contain cosmetic components such as dyes, fragrances and/or excipients, or could comprise solely the above-indicated cosmetic components in addition to the composition of the invention.

Hereinafter, non-limiting examples of base for formulations for sticks are provided, in which the term "active ingredients" may be replaced by "active ingredients plus adjuvants and/or excipients" or by "adjuvants and/or excipients".

| EXAMPLES OF COMPOSITIONS IN THE FORM OF STICK | | | | | | | | | |
|---|---|---|---|---|---|---|---|---|---|
| | parts | | | | | | | | |
| Substance | Comp. 1 | Comp. 2 | Comp. 3 | Comp. 4 | Comp. 5 | Comp. 6 | Comp. 7 | Comp. 8 | Comp. 9 |
| Cocoa butter | 65 | 70 | 75 | 80 | 68 | 72 | 75 | 78 | 76 |
| Beeswax | 14 | 16 | 11 | 5 | 11 | 16 | 12 | 7 | 9 |
| Honey | 21 | 14 | 14 | 15 | 21 | 12 | 13 | 15 | 15 |

These base compositions are mixed with the active ingredients, or active ingredients plus adjuvants and/or excipients, or adjuvants and/or excipients in final formulations containing at least 70%, at least 75%, at least 80%, at least 85%, at least 90%, at least 95% of base composition.

By way of example, and by no way of limitation, the above bases can be mixed with the active ingredients, or active ingredients plus adjuvants and/or excipients, or adjuvants and/or excipients in the following proportions:

| EXAMPLES OF COMPOSITIONS IN THE FORM OF STICK | | | | | | | | | |
|---|---|---|---|---|---|---|---|---|---|
| | parts | | | | | | | | |
| Substance | Form. 1 | Form. 2 | Form. 3 | Form. 4 | Form. 5 | Form. 6 | Form. 7 | Form. 8 | Form. 9 |
| Cocoa butter | 65 | 70 | 75 | 80 | 68 | 72 | 75 | 78 | 76 |
| Beeswax | 14 | 16 | 11 | 5 | 11 | 16 | 12 | 7 | 9 |

EXAMPLES OF COMPOSITIONS IN THE FORM OF STICK

| Substance | Form. 1 | Form. 2 | Form. 3 | Form. 4 | Form. 5 | Form. 6 | Form. 7 | Form. 8 | Form. 9 |
|---|---|---|---|---|---|---|---|---|---|
| Honey | 21 | 14 | 14 | 15 | 21 | 12 | 13 | 15 | 15 |
| Active ingredients | 14 | 15 | 4 | 3 | 5 | 7 | 2 | 4 | 0.5 |

Therefore, for instance in formulation 1 the relative percentages are: base composition abt 88%, active ingredients* abt 12%; in 2 are: base composition abt 88%, active ingredients* abt 12%; in 3 are: base composition abt 96%, active ingredients* abt 4%; in 4 are: base composition abt 97%, active ingredients* abt 3%, in 5 are: base composition abt 95%, active ingredients* abt 5%; in 6 are: base composition abt 94%, active ingredients* abt 6%; in 7 are: base composition abt 99.5%, active ingredients* abt 0.5%; in 8 are: base composition abt 98%, active ingredients* abt 4%; in 9 are: base composition abt 99.5%, active ingredients* abt 0.5%

*In the examples provided above, the term "active ingredients" may also be replaced by the term "active ingredients plus adjuvants and/or excipients" or by the term "adjuvants and/or excipients".

As already mentioned above, the formulations for topical use can also comprise adjuvants and/or excipients, or only adjuvants and/or excipients, selected according to a common formulation technique in order to make the use of the product pleasant to the consumer.

All of the examples provided above, comprising those for internal use and for oral use, may also be formulated in the form of "film" that can be poured onto medicated gauzes or plasters.

Alike in the compositions, also in the formulations unadulterated beeswax, pure cocoa butter and bee honey are used. Also the formulations, as well as the compositions, are substantially free of the cocoa butter polymorph α and/or γ.

All embodiments of the above-described compositions are to be construed as included in the embodiments of the formulations, which in fact consist of composition+active ingredients and/or adjuvants and/or excipients.

Also in the formulations of the invention, in all embodiments described, any surfactant and/or emulsifying agent is preferably absent.

One embodiment of the invention therefore relates to formulations comprising the composition of the invention+active ingredients and/or adjuvants and/or excipients in any above-indicated embodiment, characterized in that they do not contain surfactants and/or emulsifiers.

The invention also relates to a therapeutic treatment wherein a formulation according to the invention is administered to a patient in need thereof.

The invention also relates to a process for the preparation of the composition as defined in the present description and in the claims, comprising the following steps a. subjecting to co-melting, at a temperature comprised between 55° C. and 90° C., ≥0.1≤30 parts by weight of honey; ≥0.1≤17 parts by weight of beeswax; ≥65 parts by weight of cocoa butter on a total of 100 parts by weight b. cooling after pouring into suitable moulds or containers.

By "co-melting" it is meant the concomitant melting of the above-listed components, according to the present invention it can occur within a temperature range comprised between 55 and 90° C., preferably between 65 and 80° C., e.g. about 70° C. At point a. there can be subjected to co-melting all the relative parts of honey, beeswax and cocoa butter as described above with regard to the composition of the invention.

Any range or proportion among different parts described with regard to the composition of the invention and/or in the claims (wax, cocoa butter and honey) is to be considered as punctually described herein, and is to be considered as possible range or proportion among the various parts (wax, cocoa butter and honey) that can be subjected to co-melting at point a. of the above-described process.

Therefore, it can be subjected to co-melting at point a. of the above-described process any combination among >0, >0.1, >0.2, >0.3, >0.4, >0.5, >0.6, >0.7, >0.8, >0.9, 1, 2, 3, 4, 5, 6, 7, 8, 9, 10, 11, 12, 13, 14, 15, 16, 17, 18, 19, 20, 21, 22, 23, 24, 25, 28, 27, 28, 29, 30 parts by weight of honey and any intermediate number among the above-specified ones, >0, >0.1, >0.2, >0.3, >0.4, >0.5, >0.6, >0.7, >0.8, >0.9, 1, 2, 3, 4, 5, 6, 7, 8, 9, 10, 11, 12, 13, 14, 15, 16, 17 parts by weight of beeswax and any intermediate number among the above-specified ones, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and <100 parts by weight of cocoa butter and any intermediate number among the above-specified ones when the sum among those three elements is 100, wherein the sum of beeswax and honey does not exceed 35 parts by weight on 100.

Any of these combinations is to be considered as described in the present description as sufficient data are provided to easily and quickly calculate the possible combinations.

In one embodiment of the invention, the parts by weight of honey are ≥0.1, or are ≥0.5, or are ≥1, or are ≥5; or are ≥10; or are ≥15; or are ≥20; or are ≥25 and greater than or equal to any intermediate number among those indicated, or even ≥26, ≥27, ≥28, ≥29, and ≤30.

The process of the present invention, thanks to the main formula provided in claim 1, giving precise relative proportions among the three components subjected to co-melting, enables a high incorporation of honey into a mainly lipophilic base, resulting in a mass without dishomogeneities therein, therefore making pointless the aid of substances such as emulsifiers.

According to further embodiments of the invention, the parts by weight of beeswax are ≥0.1, or are ≥0.5, or are ≥1, or are ≥5; or are ≥10; or are ≥15 and greater than or equal to any intermediate number among those indicated, or even ≥16 and ≤17. Embodiments wherein the parts by weight of honey are ≥0.1, or are ≥0.5, or are ≥1, or are ≥5; or are ≥10; or are ≥15; or are ≥20; or are ≥25 and the parts by weight of beeswax are ≥0.1, or are ≥0.5, or are ≥1, or are ≥5; or are ≥10; or are ≥15 are part of the invention provided that, as evident from the above definition, the sum of beeswax and honey never exceeds 35 parts by weight on 100 of the composition.

According to a further embodiment, the parts by weight of cocoa butter are ≥70; or are ≥75; or are ≥80; or are ≥85 until reaching values anyhow <100.

In particular, the composition according to the invention comprises embodiments wherein the parts by weight of honey are ≥0.1, or are ≥0.5, or are ≥1, or are ≥5; or are ≥10; or are ≥15; or are ≥20; or are ≥25 and the parts by weight of beeswax are ≥0.1, or are ≥0.5, or are ≥1, or are ≥5; or are ≥10; or are ≥15 provided that, as evident from the above definition, the sum of beeswax and honey never exceeds 35 parts by weight on 100, and ≥70; or ≥75; or ≥80; or ≥85 parts by weight of cocoa butter.

Each of the above-indicated values for each component could be inserted as values for wax, cocoa butter and/or honey at point a. of the processes of the invention.

Object of the invention is also a process for the preparation of the pharmaceutical, veterinary or cosmetic formulation as defined in the present description and in the claims, comprising the following steps:

a. subjecting to co-melting, at a temperature comprised between 55° C. and 90° C., from ≥0.1≤30 parts by weight of honey; from ≥0.1≤17 parts by weight of beeswax; from ≥65 parts by weight of cocoa butter on a total of 100 parts by weight.

b. adding to the mixture prepared in a. one or more active ingredients and/or adjuvants and/or excipients so that said mixture prepared in a. represents at least 70%, at least 80% at least 90% or at least 95% by weight of the mixture obtained in step b.

c. cooling after pouring into suitable moulds or containers.

The co-melting temperature could be, for instance comprised in a range between 65° C. and 80° C. In one embodiment, said temperature could be of about 70° C.

The proportions at point b. may be any one of the proportions among the different components indicated for the formulations of the invention and, in case of suppositories/vaginal ovules and of oral compositions (hard or soft gelatine capsule, tablet, coated tablet) there could be had only active ingredients added at point b., or active ingredients plus adjuvants and/or excipients, whereas for the formulations for topical use, such as cutaneous or lip balm (stick) there could be had, added at point b., active ingredients, or active ingredients plus adjuvants and/or excipients or only adjuvants and/or excipients.

Hereinafter, examples are provided for the preparation of the compositions and of the formulations of the invention, and formulation examples are provided merely by way of a non-limiting example of possible embodiments of the invention.

For composition examples, reference is made to the examples already provided above.

EXAMPLES

1. Example of Preparation of Composition of the Invention.

Cocoa butter, beeswax and honey are heated at 70° C. until complete melting of the lipophilic components. Maintaining the stirring, the molten mass is poured into the moulds until cooling.

2. Example of Preparation of Formulation of the Invention.

Cocoa butter, beeswax and honey are heated at 70° C. until complete melting of the lipophilic components. The active ingredients or other substances present in the formulation as per description are added under stirring to the liquid mass, and, maintaining the stirring, the molten mass is poured into the moulds until cooling.

3. Formulation Examples in the Form of Suppositories/Vaginal Ovules

Formulative Examples of Suppositories/Vaginal Ovules

| Substance | parts | | | | | | | | |
|---|---|---|---|---|---|---|---|---|---|
| | Form. 1 | Form. 2 | Form. 3 | Form. 4 | Form. 5 | Form. 6 | Form. 7 | Form. 8 | Form. 9 |
| Cocoa butter | 65 | 70 | 75 | 80 | 85 | 69 | 73 | 82 | 85 |
| Beeswax | 15 | 10 | 10 | 10 | 10 | 15 | 9 | 7 | 5 |
| Honey | 20 | 20 | 15 | 10 + | 5 | 16 | 18 | 11 | 10 |
| Aloe, dry extract | 5 | 4 | 3 | | 4 | | 3 | | 5 |
| mallow, dry extract | 2 | | | 5 | | 3 | | | |
| glucomannan | 4 | 7 | | | | 3 | | 9 | |
| Marsh mallow, dry extract | 5 | | | 6 | | | | | 3 |
| Psyllium, powder | | | | | | 3 | | | |

4. Formulation Examples in the Form of Tablets

Formulative Examples of Tablets

| Substance | Parts | | | | | | | | |
|---|---|---|---|---|---|---|---|---|---|
| | Form. 1 | Form. 2 | Form. 3 | Form. 4 | Form. 5 | Form. 6 | Form. 7 | Form. 8 | Form. 9 |
| Cocoa butter | 65 | 70 | 75 | 80 | 85 | 66 | 73 | 82 | 85 |
| Beeswax | 16 | 15 | 10 | 10 | 10 | 4 | 9 | 7 | 5 |

-continued

| Substance | Parts | | | | | | | | |
|---|---|---|---|---|---|---|---|---|---|
| | Form. 1 | Form. 2 | Form. 3 | Form. 4 | Form. 5 | Form. 6 | Form. 7 | Form. 8 | Form. 9 |
| Honey | 19 | 15 | 15 | 10+ | 5 | 30 | 18 | 11 | 10 |
| paracetamol | 25 | | 5 | | 10 | | 15 | | 20 |
| Rice starch | 5 | 10 | | 4 | | 6 | 5 | 3 | 4 |
| talc | 2 | | 1 | | 4 | | 2 | | |
| Valerian, dry extract | | 18 | | 10 | | 25 | | 15 | |

5. Formulation Examples in the Form of Balm (Stick)

Lip Balm and Lip Stick Formulation Examples

| Substance | parts | | | | | | | | |
|---|---|---|---|---|---|---|---|---|---|
| | Form. 1 | Form. 2 | Form. 3 | Form. 4 | Form. 5 | Form. 6 | Form. 7 | Form. 8 | Form. 9 |
| Cocoa butter | 65 | 70 | 75 | 80 | 68 | 72 | 75 | 78 | 76 |
| Beeswax | 14 | 16 | 11 | 5 | 11 | 16 | 12 | 7 | 9 |
| Honey | 21 | 14 | 14 | 15 | 21 | 12 | 13 | 15 | 15 |
| Mica | 7 | 3 | | | | | | | |
| Red lake (red 7) Cl15850 | 0.75 | 10 | | | | | | | |
| Red lake (red6) Cl15650 | 7 | 2 | | | | | | | |
| Fragrance | 0.25 | 0.5 | | | | | | | |
| Allantoin | | | 4 | | | | | | |
| Sodium hyaluronate | | | | 3 | | | | | |
| Mallow extract | | | | | 4 | | | | |
| benzophenone | | | | | | 5 | | | |
| bisabolol | | | | | | 2 | | | |
| vitamin E | | | | | | | 1 | | 0.5 |
| aloe | | | | | 1 | | 1 | | |
| Menthol | | | | | | | | 1 | |
| Urea | | | | | | | | 3 | |
| Coenzyme Q10 | | | | | | | | | 1 | moisturizer sunscreen lenitive aftershave antiage

The examples reported above are merely indicative; evidently, starting from the above examples and by following the teachings of the present description, the technician in the field will know how to make other formulations and compositions falling within the object of the present invention.

The invention claimed is:

1. A composition consisting of ≥5; or ≥10; or ≥15; or ≥20; or ≥25 to ≤30 parts by weight of honey, from ≥5 to ≤17 parts by weight of beeswax, and from ≥65 parts by weight of cocoa butter for a total of 100 parts by weight.

2. The composition according to claim 1 wherein said parts by weight of beeswax are ≥10 or ≥15.

3. The composition according to claim 1 wherein said parts by weight of cocoa butter are ≥70; or ≥75; or ≥80; or ≥85.

4. The composition according to claim 1 which has a melting temperature of 36±3° C. or of 36±2° C.

5. The composition according to claim 1 which is substantially free of cocoa butter polymorph α and/or γ.

6. A method of using the composition according to claim 1 for topical or internal pharmaceutical or veterinary use, comprising administering topically or internally the composition to a human or animal.

7. The method according to claim 6 wherein said internal use is administration by an oral, vaginal, or rectal route.

8. The method according to claim 6 wherein the composition is administered in the form of a suppository, vaginal ovule, cutaneous stick, lip balm, hard or soft gelatin capsule, or tablet.

9. A base or a coating for a pharmaceutical, veterinary, or cosmetic formulation or for a medical device consisting of the composition according to claim 1.

10. A pharmaceutical, veterinary, or cosmetic formulation comprising the composition according to claim 1 and one or more active ingredients and/or adjuvants and/or excipients, wherein said composition is at least 70%, at least 80%, at least 90%, or at least 95% by weight of said formulation.

11. The formulation according to claim 10 which does not include emulsifiers and/or surfactants.

12. The formulation according to claim 10 which has a melting temperature of 36±3° C. or equal to 36±2° C.

13. The formulation according to claim 10 which is substantially free of cocoa butter polymorph α and/or γ.

14. The formulation according to claim 11 which is in the form of a film, suppository, vaginal ovule, cutaneous stick, lip balm, lipstick, hard or soft gelatin capsule, tablet, or coated tablet.

15. The formulation according to claim 14 wherein said formulation is a suppository or a vaginal ovule and comprises between 80% and 99% by weight of said composition.

16. The formulation in the form of a suppository or vaginal ovule according to claim 15 wherein said composition consists of 5 to 17 parts by weight of beeswax, 5 to 25 parts by weight of honey, and 65 to 90 parts by weight of cocoa butter for a total of 100 parts by weight.

17. The formulation in the form of a suppository or vaginal ovule according to claim 15 comprising, as active ingredients, plant extracts.

18. The formulation according to claim 14 wherein said formulation is a hard or soft gelatin capsule, tablet, or coated tablet; and comprises between 75% and 99% by weight of said composition.

19. The formulation in the form of a hard or soft gelatin capsule, tablet, or coated tablet according to claim 18 wherein said composition consists of 5 to 17 parts by weight of beeswax, 5 to 30 parts by weight of honey, and 65 to 90 parts by weight of cocoa butter for a total of 100 parts by weight.

20. The formulation in the form of a hard or soft gelatin capsule, tablet, or coated tablet according to claim 18 comprising, as active ingredients, plant extracts.

21. The formulation according to claim 14 which is in the form of a film, cutaneous stick, lip balm, or lipstick; and comprises between 80% and 99% by weight of said composition.

22. The formulation in the form of a film, cutaneous stick, lip balm, or lipstick according to claim 21 wherein said composition consists of 5 to 17 parts by weight of beeswax, 10 to 25 parts by weight of honey, and 65 to 85 parts by weight of cocoa butter for a total of 100 parts by weight.

23. The formulation in the form of a film, cutaneous stick, lip balm, or lipstick according to claim 21 comprising, as active ingredients, plant extracts, and optionally comprising dyes, fragrances, and/or excipients.

24. A process for the preparation of the composition according to claim 1 comprising:
  a. subjecting to co-melting, at a temperature comprised between 65° C. and 90° C., from $\geq 5$ to $\leq 30$ parts by weight of honey, from $\geq 5$ to $\leq 17$ parts by weight of beeswax, and from $\geq 65$ parts by weight of cocoa butter for a total of 100 parts by weight; and
  b. cooling after pouring into a suitable mould or container.

25. A process for the preparation of the pharmaceutical, veterinary, or cosmetic formulation according to claim 11 comprising:
  a. subjecting to co-melting, at a temperature comprised between 65° C. and 90° C., from $\geq 5$ to $\leq 30$ parts by weight of honey; from $\geq 5$ to $\leq 17$ parts by weight of beeswax, and from $\geq 65$ parts by weight of cocoa butter for a total of 100 parts by weight;
  b. adding to the mixture prepared in a. one or more active ingredients and/or adjuvants and/or excipients so that said mixture prepared in a. represents at least 70%, at least 80%, at least 90%, or at least 95% by weight of the mixture obtained in step b; and
  c. cooling after pouring into a suitable mould or container.

26. A method for protective treatment of skin or mucous membrane of a patient in need therefore, the method comprising administering to said patient (i) a composition consisting of $\geq 5$; or $\geq 10$; or $\geq 15$; or $\geq 20$; or $\geq 25$ to $\leq 30$ parts by weight of honey, from $\geq 5$ to $\leq 17$ parts by weight of beeswax, and from $\geq 65$ parts by weight of cocoa butter for a total of 100 parts by weight; or (ii) a formulation comprised of said composition and one or more active ingredients and/or adjuvants and/or excipients, wherein said composition is at least 70%, at least 80%, at least 90%, or at least 95% by weight of said formulation; and does not include emulsifiers and/or surfactants.

\* \* \* \* \*